United States Patent [19]

Youssefyeh et al.

[11] Patent Number: 4,831,184
[45] Date of Patent: May 16, 1989

[54] N-SUBSTITUTED-AMIDO-AMINO ACIDS

[75] Inventors: Raymond D. Youssefyeh, Tarrytown; Jerry W. Skiles, Tuckahoe, both of N.Y.; John T. Suh, Greenwich, Conn.; Howard Jones, Ossining, N.Y.

[73] Assignee: Rorer Pharmaceutical Corporation, Ft. Washington, Pa.

[21] Appl. No.: 465,940

[22] Filed: Feb. 14, 1983

Related U.S. Application Data

[63] Continuation-in-part of Ser. No. 248,172, Mar. 30, 1981.

[51] Int. Cl.$^4$ ............... C07C 101/44; C07C 69/76; C07C 69/74; C07C 61/08
[52] U.S. Cl. ..................... 560/43; 560/100; 560/123; 562/433; 562/507
[58] Field of Search ............... 260/112.5 R; 514/464; 560/43, 100, 123; 562/433, 507

[56] References Cited

U.S. PATENT DOCUMENTS 4,256,761  3/1981  Suh et al. .................. 514/464

Primary Examiner—Delbert R. Phillips

[57] ABSTRACT

This invention relates to new chemical compounds having valuable pharmaceutical activity. It particularly relates to stereoisomeric compounds possessing hypotensive activity, i.e., angiotensin converting enzyme inhibitory (ACEI) activity and having the structure

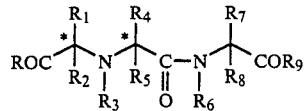

wherein R and $R_9$ are independently hydroxy, lower alkoxy, lower alkenoxy, di(lower alkyl)amino-lower alkoxy, hydroxy-lower alkoxy, acylamino-lower alkoxy, acryloxy-lower alkoxy, aryloxy, aryloxyl-lower alkoxy, amino, lower alkylamino, di-lower alkylamino, hydroxyamino, or aryl-lower alkylamino;

$R_1$, $R_2$, $R_3$, $R_4$, $R_5$, $R_7$ and $R_8$ are independently hydrogen, alkyl, alkenyl or alkynyl containing up to 20 carbon atoms, aryl or aryl-lower alkyl having from 7 to 12 carbon atoms, heterocyclic or heterocyclic-lower alkyl having from 6 to 12 carbon atoms, cycloalkyl or cycloalkyl-alkyl containing up to 20 carbon atoms in the cycloalkyl group, provided that each of $R_1$ and $R_2$ and $R_4$ and $R_5$ are different;

$R_2$ and $R_3$ taken together with the carbon and nitrogen to which they are respectively attached and $R_3$ and $R_5$ taken together with the nitrogen and carbon to which they are respectively attached form an N-heterocycle containing from 3 to 5 carbon atoms or 2 to 4 carbon atoms and a sulfur atom;

$R_6$ is cycloalkyl, polycycloalkyl, partially saturated cycloalkyl and polycycloalkyl, cycloalkyl-lower alkyl, aryl, aryl-lower alkyl, aryl-lower alkenyl, aryl-lower alkynyl; and wherein each chiral center is in the (S) configuration;

and salts thereof with acids or bases especially pharmaceutically acceptable acid and base salts.

16 Claims, No Drawings

N-SUBSTITUTED-AMIDO-AMINO ACIDS

This application is a continuation-in-part based on U.S. patent application Ser. No. 248,172 filed Mar. 30, 1981.

This invention relates to new chemical compounds having valuable pharmaceutical activity. It particularly relates to stereoisomeric compounds possessing hypertensive and angiotensin converting enzyme inhibitory activity and having the structure

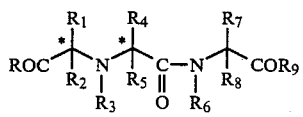

wherein

R and $R_9$ are independently hydroxy, lower alkoxy, lower alkenoxy, di(lower alkyl)amino-lower alkoxy, hydroxy-lower alkoxy, acylamino-lower alkoxy, acryloxy-lower alkoxy, aryloxy, aryloxyl-lower alkoxy, amino, lower alkylamino, di-lower alkylamino, hydroxyamino, or aryl-lower alkylamino;

$R_1$, $R_2$, $R_3$, $R_4$, $R_5$, $R_7$ and $R_8$ are independently hydrogen, alkyl, alkenyl or alkynyl containing up to 20 carbon atoms, aryl or aryl-lower alkyl having from 7 to 12 carbon atoms, heterocyclic or heterocyclic-lower alkyl having from 6 to 12 carbon atoms, cycloalkyl or cycloalkyl-alkyl containing up to 20 carbon atoms in the cycloalkyl group, provided that each of $R_1$ and $R_2$ and $R_4$ and $R_5$ are different;

$R_2$ and $R_3$ taken together with the carbon and nitrogen to which they are respectively attached and $R_3$ and $R_5$ taken together with the nitrogen and carbon to which they are respectively attached form an N-heterocycle containing from 3 to 5 carbon atoms or 2 to 4 carbon atoms and a sulfur atom;

$R_6$ is cycloalkyl, polycycloalkyl, partially saturated cycloalkyl and polycycloalkyl, cycloalkyl-lower alkyl, aryl, aryl-lower alkyl, aryl-lower alkenyl, aryl-lower alkynyl; and wherein each chiral center is in the (S) configuration;

and salts thereof with acids or bases especially pharmaceutically acceptable acid and base salts.

The alkyl groups per se or when present as substituents are preferably lower alkyl containing from 1 to 6 carbon atoms and may be straight chain or branched. These groups include methyl, ethyl, propyl, iso-propyl, butyl, isobutyl, amyl, hexyl and the like.

The alkenyl and alkynyl groups per se or when present as substituents preferably contain from 2 to 6 carbon atoms and may be straight chain or branched. These groups include vinyl, propenyl, allyl, isopropenyl, ethynyl and the like.

The alkyl, alkenyl, and alkynyl groups may carry substituents such as hydroxy, lower alkoxy, thio, lower alkylmercapto, amino, lower alkylamino, di(lower alkyl) amino, halogen, and nitro.

The aryllower alkyl and heterocycliclower alkyl groups include benzyl, phenethyl, napthylmethyl, indolylethyl, indanylmethyl, indanylethyl and the like.

The cycloalkyl groups may be mono or polycyclic and contain from 3 to 20 carbons. These groups include cyclopropyl, cyclopentyl, cyclohexyl, cycloheptyl, bornyl, nor-bornyl, indanyl and the like. These groups may be partially unsaturated and carry substituents such as halogen, hydroxy, lower alkyl, lower alkoxy, amino lower alkylamino, di (lower alkyl) amino, thiol, lower alkylmercapto, nitro, and trifluoromethyl.

The aryl groups contain from 6 to 10 carbon atoms and include such groups as phenyl and α or β-naphthyl and fused phenyl-cycloalkyl such as indanyl.

The aryl and aralkyl groups may carry one or more substituents such as lower alkyl, lower alkenyl, lower alkynyl, hydroxy, lower alkoxy, amino, lower alkylamino, di(lower alkyl)-amino, thiol, lower alkylmercapto, hydroxy-lower alkyl, amino-lower alkyl, thio-lower alkyl, nitro, halogen, trifluoromethyl, methylenedioxy, ureido, or guanidino.

The acyl groups are preferably lower alkanoyl containing from 1 to 6 carbon atoms and benzoyl.

The halogen group may be fluorine, chlorine, bromine and iodine.

Suitable acid addition salts may be formed from inorganic acids such as hydrochloric, sulfuric and phosphoric, and organic acids such as acetic, lactic, citric, malic, maleic, fumaric, succinic, benzoic, hydroxybenzoic, aminobenzoic, nicotinic, toluene sulfonic and the like.

Suitable basic salts may include the salts of alkali and alkali earth metals such as sodium, lithium, potassium, magnesium and calcium, as well as iron and salts of ammonia and amines, and quaternary ammonium salts.

The compounds of the present invention contain two or three asymmetric carbon atoms in which the chiral centers are each in the (S) configuration.

The compounds of the present invention are preferably prepared by stereospecific amide-forming reaction of a compound of the formula:

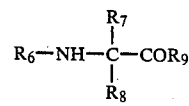

with an acylating derivative of an acid of the formula

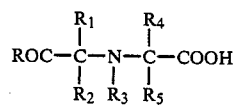

to obtain a single stereoisomeric product. Of course where $R_7$ and $R_8$ of compounds of formula III differ a further chiral center exists at the carbon atom to which they are attached and, in accordance with the present invention, this chiral center is preferably in the (S) configuration.

The present new compounds can also be prepared by using a mixture of the stereoisomers, (R) and (S), of compounds of formula III, followed by resolution of the mixture of isomers, (SSR) and (SSS) so produced. However, such synthesis is not preferred in view of the necessity of resolution of the resulting product mixture.

Further, the present new compounds can be prepared by condensation reaction of a compound of the formula:

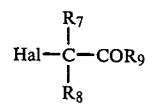

in which Hal is halogen, a compound of the formula:

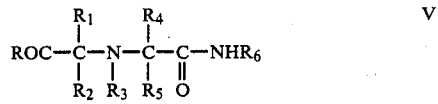

by cleavage of hydrogen halide. In this synthesis, the product where a mixture of (SSR) and (SSS) stereoisomers must be subjected to resolution procedures to recover the desired (SSS) isomer.

As an alternative approach, a dipeptide of the structure

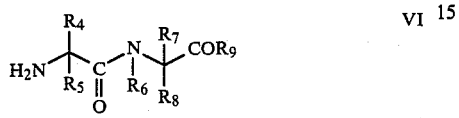

is reacted with an -keto-acid or ester of the structure

to form the corresponding imine and the imine is reduced to give a compound of formula I in which $R_2$ and $R_3$ are each H.

In the above sequence of reactions, R -$R_9$ are the same as described above and Hal is halogen.

Preferably, R and $R_9$ are hydrogen or lower alkyl, $R_2$, $R_5$, $R_7$ and $R_8$ are hydrogen, $R_1$ and $R_4$ are lower alkyl, $R_3$ is hydrogen, and $R_6$ is cycloalkyl, aryl, and aralkyl.

The amide forming conditions referred to herein involve the use of known derivatives of the described acids, such as the acyl halides, anhydrides, mixed anhydrides, lower alkyl esters, carbodiimides, carbonyl diimidazoles, and the like. The reactions are carried out in organic solvents such as acetonitrile, tetrahydrofuran, dioxane, acetic acid, methylene chloride, ethylene chloride and similar such solvents. The amide forming reaction will occur at room temperature or at elevated temperature. The use of elevated temperature is for convenience in that it permits somewhat shortened reaction periods. Temperatures ranging from 0° C. up to the reflux temperature of the reaction system can be used. As a further convenience the amide forming reaction can be effected in the presence of a base such as tertiary organic amines, e.g., trimethylamine, pyridine, picolines and the like, particularly where hydrogen halide is formed by the amide-forming reaction, e.g., acyl halide and amino compound. Of course, in those reactions where hydrogen halide is produced, any of the commonly used hydrogen halide acceptors can also be used.

In the condensation of an alpha haloacid derivative of formula VIII herein, similar reaction conditions, solvents and hydrogen halide acceptors can be used as for amide formation.

Various substituents on the present new compounds, e.g., as defined for $R_8$, can be present in the starting compounds or added after formation of the amide products by the known methods of substitution or conversion reactions. Thus, the nitro group can be added to the final product by nitration of the aromatic ring and the nitro group converted to other groups, such as amino by reduction, and halo by diazotization of the amino group and replacement of the diazo group. Other reactions can be effected on the formed amide product. Amino groups can be alkylated to form mono and dialkylamino groups, mercapto and hydroxy groups can be alkylated to form corresponding ethers. Thus, substitution or alteration reactions can be employed to provide a variety of substituents throughout the molecule of the final products. Of course, reactive groups where present should be protected by suitable blocking groups during any of the aforesaid reactions particularly the condensation reactions to form the amide linkages.

The acid and base salts of the present new compounds can be formed using standard procedures. Often they are formed in situ during the preparation of the present new amido amino acids.

The compounds of formula III herein are new compounds which are particularly valuable is essential intermediates in the stereospecific synthesis of the valuable therapeutic compounds of formula I herein as well as other therapeutic agents such as those in which $R_6$ and $R_8$ together with the carbon and nitrogen to which they are respectively attached form a tetrahydroisoquinoline, dihydroindole, or pyrrolidine ring. Particularly preferred are compounds in which $R_1$ is phenethyl or of the formula:

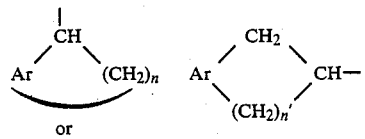

wherein
n=2, 3 or 4
n=1, 2 or 3; and
Ar is arylene or substituted arylene containing one or two substituents such as halo, $CF_3$, lower alkyl, OH, lower alkoxy, mercapto, amino or sulfanyl.

The therapeutic compounds of formula I herein in the (SS) or (SSS) stereochemical configuration are of especially valuable therapeutic properties and are more desirable for therapeutic use as angiotensin converting enzyme inhibitors in the treatment of hypertension than corresponding compounds wherein one or more chiral centers is in the (R) configuration.

The compounds of the present invention demonstrate potent activity in inhibiting angiotensin converting enzyme (ACEI activity) and may be administered orally or parenterally in the treatment of hypertension. It is within the skill of the practioner to determine the amount to be administred. Suitable dosage forms include tablets, capsules, elixirs and injectables.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The precentage of the compositions and preparations may, of course be varied and may conveniently be between about 2 to about 60% of the weight of the unit. The amount of active compound in such therapeutically useful compositions is such that a suitable dosage will be obtained. Preferred compositions or preparation according to the present invention are prepared so that an oral dosage unit form contains between about 50 and 300 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions or suspensions of the active compound or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The present new dipeptide compounds are therapeutically useful as such or can be employed in the form of salts with either acids or bases. Thus, these compounds form salts with a wide variety of acids and bases, inorganic and organic, including therapeutically-acceptable acids and bases. The therapeutically-acceptable salts are, of course, useful in the preparation of formulations where water solubility is desired. The therapeutically-acceptable salts are particularly useful in the isolation and purification of the present new compounds. Therefore, all such salts of the present new compounds are contemplated by the present invention.

The pharmaceutically-acceptable salts are of particular value in therapy. These include salts formed with mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, succinic, arylsulfonic, e.g. p-toluenesulfonic acids, and the like; as well as metal salts such as Na, K, Ca, Mg salts formed by reaction with suitable basic compounds of said metals. The pharmaceutically-unacceptable salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

The invention is further illustrated by the following examples.

EXAMPLE 1

Synthesis of N-[1-(S)-Ethoxycarbonyl-1-(2,3-dihydro-1H-inden-2-yl)-methyl]-L-alanyl-N-(2,3-dihydro-1H-inden-2-yl)-glycine

A.

N-[1-(S)-Ethoxycarbonyl-1-(2,3-dihydro-1H-inden-2-yl)-methyl]-(L)-alanine benzyl ester Benzyl R-2-iodopropionate (obtained from 36.8 gms of the corresponding bromo compound by reaction with NaI/acetone) is dissolved in 350 ml of acetonitrile and 22 ml of triethylamine. Ethyl S-amino-2,3-dihydro-1H-inden-2-yl acetate hydrochloride (21.5 g) is added and refluxed overnight. After concentrating, it is taken up in ethyl acetate, and washed 3 times with H$_2$O, 5% Na$_2$S$_2$O$_3$, and brine and the organic layer dried over MgSO$_4$, filtered and concentrated. HPLC chromatography with CH$_2$Cl$_2$ gives 15 gms. Washing the column with EtOAc allows the recovery of starting amino ester.

B.

N-[1-(S)-Ethoxycarbonyl-1-(2,3-dihydro-1H-inden-2-yl)methyl]-(S)-alanine

To 15 gms of the product of paragraph A in 250 ml of ethanol is added 1.5 g of 5% Pd/C. This mixture is hydrogenated overnight to obtain the product.

C.

N-[1-(S)-Ethoxycarbonyl-1-(2,3-dihydro-1H-inden-2-yl)methyl]-(S)-alanyl-N-carboxy-anhydride The product of paragraph B (5.0 g) is suspended in dry THF (25 ml) and then placed under nitrogen. An excess of phosgene (12.5% in toluene, obtained from MCB) is added portionwise. The resulting mixture is stirred for five minutes at room temperature and then heated to a gentle reflux for two and a half hours. All material dissolves upon the first addition of phosgene. The solvent is evaporated and the N-carboxy-anhydride is used directly in the next reaction without further purification.

D. tert-Butyl N-(2,3-dihydro-1H-inden-2-yl)glycinate hydrochloride

Acetonitrile (800 ml) is added to 2-aminoindan hydrochloride (50 g, 0.295 mole) followed by the addition of water (100 ml) and concentrated ammonium hydroxide (100 ml). To the resulting stirring solution tert-butyl bromoacetate (60 g, 0.308 mole) in acetonitrile (150 ml is added dropwise at room temperature and the resulting mixture stirred overnight at room temperature. The acetonitrile is evaporated on a rotary evaporator, water added to the residue and the product extracted several times into methylene chloride. The combined methylene chloride extract is washed twice with water, dried over magnesium sulfate, filtered and evaporated to afford the crude product as a tan oil. The crude product is purified further by silica-gel chromatography (chloroform). The desired fractions are concentrated and the hydrochloride prepared with ether-hydrochloric acid to afford tert-butyl N-(2,3-dihydro-1H-inden-2-yl)glycinate hydrochloride as a colorless solid (60 g, 72%); m.p. 175°; mass spectra (CI): 248(m+1, 100%).

E. tert-Butyl N-[1-(S)-ethoxycarbonyl-1-(2,3-dihydro-1H-inden-2-yl)methyl]-(S)-alanyl-N-(2,3-dihydro-1H-inden-2-yl)glycinate To the cuude carboxyanhydride of paragraph C in methylene chloride (100 ml) is added tert-butyl N-(2,3-dihydro-1H-inden-2-yl)glycinate (5.5 g, 22.3 mmoles). The resulting solution is stirred overnight at room temperature, the solvent evaporated and the residue chromatographed over silica-gel using ethyl acetate/n-hexane (3:6) as eluent. The desired fractions are combined and concentrated to give the product.

F. N-[1-(S)-Ethoxycarbonyl-(2,3-dihydro-1H-inden-2-yl)methyl]-(S)-alanyl-N-(2,3-dihydro-1H-inden-2-yl]glycine hydrochloride To the product of paragraph E (1.4 g) is added p-dioxane saturated with anhydrous hydrogen chloride (35 ml). The resulting solution is stirred for two and a half hours at room temperature and the solvent then evaporated to afford a colorless solid. Anhydrous diethyl ether is added to the residue and the product filtered and washed with a small amount of ether to obtain the product as the hydrochloride salt.

EXAMPLE 2

A. t-Butyl N-carbobenzoxy-L-alanyl-N-(5-indanyl)glycidate

To a solution of t-butyl N-(5-indanyl)glycinate (24.5 g, 99.1 mmol) and dicyclohexylcarbiimide (20.4 g, 99.1 mmol) in 130 ml of methylene chloride was added dropwise a solution of N-carbobenzoxy-L-alanine (22.1 g, 99.1 mmol) in 150 ml methylene chloride. After the addition was complete the solution stirred 18h, filtered and concentrated in vacuo. The residue was diluted with ether, filtered, washed with aqueous acid, aqueous NaOH and dried (MgSO$_4$). Removal of the volatiles in vacuo and chromatography on silica-gel using 10% ethyl acetate in hexanes as eluents provided the oily product.

B. t-Butyl L-analyl-N-(5-indanyl)glycinate

To a solution of t-butyl N-carbobenzoxy-L-alanyl-N-(5-indanyl)-glycinate (7.35 g, 16.3 mmol) and ammonium formate (3.09 g, 48.9 mmol) in 110 ml methanol was added 2.70 g of 10% palladium on carbon. The mixture was stirred for 10 minutes, filtered and concentrated in vacuo. Thr residue was partitioned between ether and water. The aqueous layer was saturated with sodium chloride and extracted thoroughly with methylene chloride. The combined organic extracts were dried (MgSO$_4$) and concentration in vacuo to provide the crystalline product.

C. t-Butyl N-(1-(S)-ethoxycarbonyl-3-phenylpropyl)-L-alanyl-N-(5-indanyl)glycinate A solution of t-butyl L-alanyl-N-(5-indanyl) glycinate (4,80 g, 15.09 mmol), ethyl 4-phenyl-2-oxobutyrate (15.50 g, 75.47 mmol) and 30 g of powdered 3A molecular sieves in 100 ml absolute ethanol was stirred 60 minutes, at which time sodium cyanoborohydride (1.05 g, 16.6 mmol) in 15 ml absolute ethanol was added dropwise over the course of 90 minutes. After the addition was complete the solution stirred 18 h, filtered and concentrated in vacuo. Chromatography of the residue on silica-gel using 20% ethyl acetate in hexanes as eluents provided the desired diastereomer as an oil.

D.
(1-(S)-Ethoxycarbonyl-3-phenylpropyl)-L-alanyl-N-(5-indanyl)-glycine maleate salt To 2.30 gm of t-butyl N-(1-(S)-ethoxycarbonyl-3-phenylpropyl-L-alanyl-N-(5-indanyl)glycinate in 8 ml acetic acid at 0° C. under $N_2$ was added 5ml of 3.5 N HBr in acetic acid. The solution was kept cold for 10 minutes, warmed to room temperature and stirred 20 minutes. The solution was concentrated in vacuo at 35° C. The residue was dissolved in 1:1 ethanol-water, cooled with an ice bath and neutralized with aqueous NaOH. The solution was applied to a Dowex 50×2−100 (50 g) column and eluted first with 1:1 ethanol-water and 3% pyridine in water. The product rich fractions were lyophilized. The residue (1.340 g) was dissolved in 5 ml acetonitrile and maleic acid (0.3439 g) in 10 ml acetonitrile was added. The solution was concentrated in vacuo. The residue was crystallized from ethyl acetate with hexanes. Trituration of the solid with ether and hexanes provided the crystalline salt. (mp 64° C. (softens)).

EXAMPLE 3

A. tert-Butyl N-(β-phenylethyl)glycinate hydrochloride

Acetonitrile (800 ml) was added to β-phenethyl amine (50 g, 0.413 mole) followed by the addition of water (100 ml) and concentrated ammonium hydroxide (75 ml). To the resulting stirring solution tert-butyl bromoacetate (82 g, 0.421 (mole) in acetonitrile (150 ml) was added dropwise at room temperature. The resulting mixture was stirred overnight at room temperature. The acetonitrile was evaporated on a rotary evaporator and then water was added to the residue and the product was extracted several times into methylene chloride. The combined methylene chloride extract was washed twice with water, dried over magnesium sulfate, filtered and evaporated to afford the crude product as a tan oil. The crude product was purified further by silica-gel chromatography (chloroform). The desired fractions were concentrated and the hydrochloride was prepared with anhydrous hydrogen chloride in ether to give tert-butyl N-(β-phenylethyl) glycinate hydrochloride as a colorless solid (62 g, 55%); m.p. 143°; mass spectra (CI): 143.8 (30.84%); 133.8 (40.93%); 104.8 (38.33%; 87.8 (100%).

B. tert-Butyl N-[1-(S)-ethoxycarbonyl-3-phenylpropyl]-(S)-alanyl-N-(β-phenylethyl) glycinate To crude N-[1-(S)-ethoxycarbonyl-3-phenylpropyl-(S)-alanyl-N-carboxyanhydride which had been prepared from 5 grams of the corresponding (SS)-acid in methylene chloride was added tert-butyl N-(β-phenylethyl) glycinate (5 g, 21.3 mmole). The resulting solution was stirred overnight at room temperature. The solvent was evaporated and the residue was chromatographed over silica-gel using chloroform as eluent. The desired fractions were combined and concentrated to give pure tert butyl N-[1-(S)-ethoxycarbonyl-3-phenylpropyl]-(S)-alanyl-N-(β-phenylethyl) glycinate (6.2 g, 69.7%) as a pale yellow oil; mass spectra (CI): 497 (m+1, 52%); 350 (100%).

C.
N-[1-(S)-Ethoxycarbonyl-3-phenylpropyl]-(S)-alanyl-N-(β-phenethyl)glycine hydrochloride To tert-butyl N-[1-(S)-ethoxycarbonyl-3-phenylpropyl]-(S)-alanyl-N-(β-phenyethyl) glycinate (2 g, 4.03 mmoles) was added p-dioxane which had been saturated with anhydrous hydrogen chloride (75 ml). The resulting solution was stirred for three hours at 45° and then the solvent was evaporated to afford N-[1-(S)-ethoxycarbonyl-3-phenylproply]-(S)-alanyl-N-(β-phenethyl)glycine hydrochloride as a colorless powder (1.62 g, 84.2%): m.p. 72°; $[\alpha]_D CHCL_3 = +10.95°$; mass spectra (CI): 423 (m+1−$H_2O$, 100%) .

Analysis calculated for $C_{25}H_{32}N_2O_5.HCl.\frac{1}{2}H_2O$: 61.78; H, 7.05; N, 5.77. Found: C, 61.37; H, 6.71; N, 5.15.

EXAMPLE 4

N-[1-(S)-Ethoxycarbonyl-1-(2,3-dihydro-1H-inden-2-yl)methyl]-(S)-alanyl-(N'-2,3-dihydro-1H-inden-2-yl)glycine Using examples given above, N-[1-(S)-Ethoxycarbonyl-1-(2,3-dihydro-1H-inden-2-yl)methyl]-(S)-alanine and N-2,3-dihydro-1H-inden-2-ylglycine benzyl ester are reacted and the resulting benzyl ester is treated with hydrogen in the presence of palladium on charcoal to give the title compound.

EXAMPLE 5

A. tert-Butyl N-(20 indanyl) glycinate hydrochloride

Acetonitrile (800 ml) was added to 2-aminoindan hydrochloride (50 g, 0.295 mole) follwed by the addition of water (100 ml) and concentrated ammonium hydroxide (100 ml). To the resulting stirring solution tert-butyl bromoacetate (60 g, 0.308 mole) in acetonitrile (150 ml) was added dropwise at room temperature. The resulting mixture was stirred overnight at room temperature. The acetonitrile was evaporated on a rotary evaporator and then water was added to the residue and the product was extracted several times into methylene chloride. The combined methylene chloride extract was washed twice with water, dried over magnesium sulfate, filtered and evaporated to afford the crude product as to a tan oil. The crude product was purified further by silica-gel chromatography (chloroform). The desired fractions were concentrated and the hydrochloride was prepared with ether-hydrochloric acid to afford tert-butyl N-(2-indanyl)glycinate hydrochloride as a colorless solid (60 g; m.p. 175°; mass spectra (CI): 248 (m+1,100%).

B.
N-[1-(S)-Ethoxycarbonyl-3-phenylpropyl]-(S)-alanyl-N-carboxyanhydride

N-[1-(S)-Ethoxycarbonyl-3-phenylpropyl]-(S)-alanine (50 g, 1.9 mmole) was suspended in dry THF (25 ml) and then placed under nitrogen. An excess of phosgene (12.5% in toluene) was added portionwise. The resulting mixture was stirred for five minutes at room temperature and then heated to a gentle reflux for two and a half hours. All material dissolved upon the first addition of phosgene. The solvent was evaporated and the residue was placed under high vacuum (oil pump) upon which time the N-carboxyanhydride (NCA) crystallized. The N-carboxyanhydride was used directly in the next reaction without further purification.

C. tert-Butyl N-[1-(S)-ethoxycarbonyl-3-phenylpropyl]-(S)-alanyl-N-(2-indanyl)glycinate To crude N-[1-(S)-ethoxycarbonyl-3-phenylpropyl]-(S)-alanyl-N-carboxyanhydride, which had been prepared from 5 grams of the coreesponding (SS)-acid; in methylene chloride (100 ml) was added tert-butyl N-(2-indanyl)glycinate (5.5 g, 22.3 mmoles). The resulting solution was stirred overnight at room temperature. The solvent was evaporated and the residue was chromatographed over silica-gel using ethyl acetate/n-hexane (3:6) as eluent. The desired fractions were combined and concentrated to give pure tert-butyl N-[1-(S)-ethoxycarbonyl-3-phenylpropyl[-(S)-alanyl-N-(2-indanyl)-glycinate as a pale yellow oil (1.6 g, 16%); mass spectra (CI): 509 (m+1,100%).

D. N-[1-(S)-Ethoxycarbonyl-3-phenylpropyl[-(S)-alanyl-N-(2-indanyl)glycine hydrochloride To tert-butyl N-[1-(S)-ethoxycarbonyl-3-phenyl-propyl]-(S)-alanyl-N-(2-indanyl)glycinate (1.4 g, 2.75 mmoles) was added p-dioxane which had been saturated with anhydrous hydrogen chloride (35 ml). the resulting solution was stirred for two and a half hourst at room temperature and then solvent was evaporated to afford a colorless solid. Anhydrous diethyl ether was added to the residue and the product was filtered and washed with a small amount of ether to give N-[1-(S)-ethoxycarbonyl-3-phenylpropyl]-(S)-alanyl-N-(2-indanyl)glycine hydrochloride (1.1 g, 84.6%) as a colorless solid: m.p. 181°; $[\alpha]_D ETOH = +16.44°$; mass spectra (CI): 435.6(m+1−H$_2$O, 100%).

EXAMPLE 6

N-[1-(S)-Ethoxycarbonyl-1-(2,3-dihydro-1H-inden-2-yl]methyl[(S)-(4-pyridyl)alanyl]glycine Using examples given above, N-[1-(S)-Ethoxycarbonyl-1-(2,3-dihydro-1H-inden-2-yl)-methyl]-(S)-(4-pyridy)alanine and glycine benzyl ester are reacted and the resulting benzyl ester treated with hydrogen in the presence of palladium on carbon to give the title compound.

Employing the foregoing procedures the following compounds are prepared from corresponding starting materials:

N-[1-(S)-Ethoxycarbonyl-1-(2,3-dihydro-1H-inden-1-yl)methyl]-L-alanine

N-[1-(S)-Methoxycarbonyl-1-(2,3-dihydro-1H-inden-2-yl)methyl]-L-alanine

The following dipeptide compounds in the (S)-configuration at each chiral center are prepared employing the procedures of the preceding examples from corresponding intermediates:

N-(2,3-Dihydro-1H-inden-5-yl)-N-[N-[1.(S)-ethoxycarbonyl-1-(2,3-dihydro-1H-inden-2-methyl]-(S)-alanyl]glycine N-Cyclopentyl-N[N-[1-(S)-ethoxycarbonyl-1-(2,3-dihydro-1H-inden-2-yl)-methyl]-(S)-alanyl]glycine N-(2,3-dihydro-1H-inden-5-yl)-N-[N-(1S)-lethoxycarbonyl-1-(2,3-dihydro-1H-inden-2-yl)-methyl[-L-alanyl]glycine N-Cyclopentyl-N-[N-(1S)-1-ethoxycarbonyl-1-(2,3-dihydro-1H-inden-2-yl)-methyl]-L-alanyl]glycine N-[1-(S)-Ethoxycarbonyl-1-(2,3-dihydro-1H-inden-2-yl)methyl]-(S)-alanyl-N-1-(2,3-dihydro-1H-inden-1-yl)glycine 2-N-[1-(S)-Ethoxycarbonyl-1-(2,3-dihydro-1H-inden-1-yl)methyl]-(S)-alanyl-N-1-(2,3-dihydro-1H-inden-2-yl)-S-alanine N-[1-(S)-Ethoxycarbonyl-2-phenylethyl]-L-alanyl-N-(indanyl)glycine N-[1-(S)-Ethoxycarbonyl-3-methylbutyl]-L-valyl-N-(p-bromophenyl)glycine N-[1-(S)-Ethoxycarbonyl-3-phenylpropyl]-L-isoleucyl-N-[(2-chloro-5-methoxy)phenyl]glycine N-[1-(S)-Ethoxycarbonyl-3-methylthiopropyl]-L-alanyl-N-(3-cyano-phenyl)-glycine N-[1-Ethoxycarbonyl-4-methylpentyl]-L-alanyl-N-(3,4-dimethoxybenzyl)-L-alanine N-[1-(S)-Ethoxycarbonyl-3-phenylpropyl]-L-alanyl-N-(3,5-dimethylphenyl)glycine N-[1-(S)-Ethoxycarbonyl-2-(3-indolyl)ethyl]-L-valyl-N-(m-tolyl)glycine N-[1-(S)-Ethoxycarbonylethyl](p-chlorophenylalnyl)-N-(m-trifluoromethylphenyl)glycine N-[1-Ethoxycarbonyl-3-methylbutyl]-L-alanyl-N-(m-methoxyphenyl)glycine N-[1-(S)-Ethoxycarbonylhexyl]-L-phenylalanyl-N-(p-isopropylphenyl)glycine N-[1-(S)-Ethoxycarbonyl-3-phenylpropyl]-L-isoleucyl-N-]p-(n-butyl-phenyl)]glycine N-[1-(S)-Ethoxycarbonylethyl]-L-methionyl-N-(4-t-butyl-phenyl)-L-alanine N-[1-(S)-carboxyethyl]-L-valyl-N-(3-methylthio-phenyl)-L-alanine N-[1-(S)-Carboxy-3-phenylpropyl]-L-alanyl-N-(α-napthyl)glycine N-[1-(S)-Ethoxycarbonyl-2-phenylethyl]-L-phenylalanyl-N-(2-chlorobenzyl)glycine N-[1-(S)-Carboxy-3-methylbutyl]-L-alanyl-N-(3,4-dihydroxyphenethyl)glycine N-[1-(S)-Ethoxycarbonyl-3-phenylpropyl]-L-alanyl-N-(o-carboxy phenyl)glycine N-[1-(S)-Carboxy-2-phenylethyl]-L-valyl-N-(m-biphenyl)glycine The dipeptide compounds demonstrate high angiotensin converting enzyme inhibition, (ACEI activity) which is of substantially long duration particularly those compounds with a fused arylcycloalkyl in place of an aralkyl grouip as substituent R$_1$ and especailly as the substituent R$_6$ on the glycine nitrogen.

The compounds may be administered orally or parenterally in the treatment of hypertension and it is within the professional judgment and skill of the practitioner to determine the amount to be administered. Suitable dosage forms include tablets, capsules, elixirs and injectables.

We claim:
1. A compound of the formula

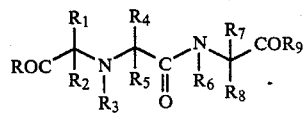

wherein each of the chiral centers are in the (S) configuration;

R and R$_9$ are independently hydroxy or lower alkoxy;

R$_1$ and R$_2$ are hydrogen or lower alkyl, aryl-lower alkyl having from 7 to 12 carbon atoms, or heterocyclic-lower alkyl having from 6 to 12 carbon atoms, $R_3$, $R_4$, $R_5$, $R_7$ and $R_8$ are hydrogen or lower alkyl, provided that at least $R_1$ and $R_2$ and $R_4$ and $R_5$ are different;

$R_6$ is cycloalkyl, polycycloalkyl, partially saturated cycloalkyl and polycycloalkyl, cycloalkyl-lower alkyl having from 3 to 20 carbon atoms, aryl or aryl-lower alkyl, and the aryl group contains from 6 to 10 carbon atoms wherein the aryl groups can be substituted by lower alkyl, lower alkenyl, lower alkynyl, hydroxy, lower alkoxy, amino, lower alkylamino, di(lower alkyl)amino, thiol, lower alkylmercapto, hydroxy-lower alkyl, amino-lower alkyl, thio-lower alkyl, nitro, halogen, trifluoromethyl, methylenedroxy, ureido and guanidino, and salts thereof especially pharmaceutically acceptable acid and base salts.

2. A compound according to claim 1 wherein $R_1$ is lower alkyl or aryl-lower alkyl, $R_4$ is lower alkyl, and $R_2$, $R_3$, $R_5$, $R_7$ and $R_8$ are hydrogen.

3. A compound according to claim 2 wherein R and $R_9$ are hydroxy.

4. A compound according to claim 2 wherein R is ethoxy and $R_9$ is hydroxy.

5. A compound according to claim 4 wherein $R_1$ and $R_4$ are methyl.

6. A compound according to claim 4 wherein $R_1$ is phenethyl and $R_4$ is methyl.

7. A compound according to any one of claims 1–6 wherein $R_6$ is indanyl.

8. A compound according to any one of claims 1–6 wherein $R_6$ is 2-indanyl.

9. A compound according to any one of claims 1–6 wherein $R_6$ is 5-indanyl.

10. N-[1-(S)-Ethoxycarbonyl-1-(2,3-dihydro-1H-inden-2-yl)-methyl]-L-alanyl-N-(2,3-dihydro-1H-inden-2-yl-glycine.

11. N-(1-(S)-Ethoxycarbonyl-3-phenylpropyl)-L-alanyl-N-(5-indany)glycine.

12. N-[1-(S)-ethoxycarbonyl-3-phenylpropyl]-(S)-alanyl-N-(β-phenethyl)glycine.

13. An acid salt of the compound of N-[1-(S)-Ethoxycarbonyl-1-(2,3-dihydro-1H-inden-2-yl)-methyl]-L-alanyl-N-(2,3-dihydro-1H-inden-2-yl-glycine.

14. An acid salt of the compound of N-(1-(S)-Ethoxycarbonyl-3-phenylpropyl)-L-alanyl-N-(5-indanyl) glycine.

15. An acid salt of the compound of N-[1-(S)-ethoxycarbonyl-3-phenylpropyl]-(S)-alanyl-N-(β-phenethyl) glycine.

16. N-[1-(S)-ethoxycarbonyl-3-phenylpropyl]-(S)-alanyl-N-(2-indanyl) glycine and the pharmaceutically acceptable salts thereof.

* * * * *